(12) United States Patent
Miller

(10) Patent No.: US 6,335,006 B1
(45) Date of Patent: Jan. 1, 2002

(54) METHODS OF USING AGENTS THAT ACT ON THE EPITHELIAL SHEET OF A HUMAN EYE

(75) Inventor: David Miller, Brookline, MA (US)

(73) Assignee: Boston Innovative Optics, Inc., Irvine, CA (US)

( * ) Notice: Subject to any disclaimer, the term of this patent is extended or adjusted under 35 U.S.C. 154(b) by 0 days.

(21) Appl. No.: 09/528,459

(22) Filed: Mar. 17, 2000

Related U.S. Application Data

(60) Provisional application No. 60/125,387, filed on Mar. 22, 1999.

(51) Int. Cl.$^7$ .............................................. A61K 31/47
(52) U.S. Cl. .................................... 424/78.04; 514/912
(58) Field of Search ........................ 514/912; 424/78.04

(56) References Cited

U.S. PATENT DOCUMENTS

| | | | |
|---|---|---|---|
| 5,270,051 A | 12/1993 | Harris et al. ................. | 424/427 |
| 5,626,865 A | 5/1997 | Harris et al. ................. | 424/427 |
| 5,788,957 A | 8/1998 | Harris et al. ............. | 424/78.04 |
| 5,866,120 A | 2/1999 | Karageozian et al. .... | 424/94.62 |

FOREIGN PATENT DOCUMENTS

| | | | | |
|---|---|---|---|---|
| WO | WO 91/16070 | 10/1991 | .......... | A61K/37/54 |
| WO | WO 98/52602 | 11/1998 | .......... | A61K/38/47 |
| WO | WO 99/40933 | 8/1999 | .......... | A61K/38/46 |

OTHER PUBLICATIONS

PCT/ISA/220 PCT International Search Report PCT/US00/07253 17.10.00.
Gipson et al. "A technique for obtaining sheets of intact rabbit corneal epithelium" *Investigative Ophthamology & Visual Science*, vol. 23:269–273 Aug. 1982.
Gipson et al. "Hemidesmosome Formation In Vitro" *The Journal of Cell Biology*, vol. 97:849–857 Sep. 1983.
Gipson et al. "Transplant of Corneal Epithelium to Rabbit Corneal Wounds In Vivo" *Investigative Ophthamology & Visual Science*, vol. 26:425–433, Apr. 1985.
Nezu et al. "Flow Cytometry Cell–cycle Analysis for in vivo Corneal Epithelium" *Acta Societatis Ophthamologicae Japonie*, vol. 96:283–287 1992.
Inoue et al. "the Effect of Hyaluronic Acid on Corneal Epithelial Cell Proliferation" *Investigative Ophthamology & Visual Science*, vol. 34:2313–2315 Jun. 1993.
Lindberg et al. "In Vitro Propagation of Human Ocular surface Epithelial Cells for Transplantation" *Investigative Ophthamology & Visual Science*, vol. 34:2672–2679 Aug. 1993.
Meller et al. "A Modified Technique of Impression Cytology to Study the Fine Structure of Corneal Epithelium" *Ophthamalic Research*, vol. 28:71–79 1996.
Ren et al. "Apoptosis in the Corneal Epithelium" *Investigative Ophthamology & Visual Science*, vol. 37:1017–1025 May 1996.
Paugh et al. "Preservative Effect on Epithelial Barrier Function Measured with a Novel Technique" *Lacrimal Gland, Tear Film, and Dry Eye Syndromes*, vol. 2:731–735 1998.
Cimberle "LASEK may offer the advantages of both LASIK and PRK" *Ocular Surgery News*, p. 28 Mar. 1, 1999.

*Primary Examiner*—Zohreh Fay
(74) *Attorney, Agent, or Firm*—Bromberg & Sunstein LLP

(57) ABSTRACT

A method of delaminating the epithelial sheet of the cornea of a human eye comprising loosening the epithelial sheet with a loosening solution, the loosening solution including an agent, and separating the loosened epithelial sheet from the underlying tissue of the cornea. In the alternative, a method of delaminating the epithelial sheet from the cornea of a human eye comprising making an incision in the epithelial sheet, loosening the incised epithelial sheet using a loosening solution, the loosening solution including an agent, and separating the loosened epithelial sheet from the underlying tissue of the cornea. In addition, a method of administering a medicine through the epithelial sheet of the cornea of a human eye comprising applying a treatment solution of the medicine to the eye, the treatment solution including an agent.

41 Claims, 5 Drawing Sheets

METHODS OF USING AGENTS THAT ACT ON THE EPITHELIAL SHEET OF A HUMAN EYE

This application claims priority from provisional patent application 60/125,387, filed Mar. 22, 1999, entitled CHEMICAL METHOD OF REMOVING HEALTHY CORNEAL EPITHIELIUM, the disclosure of which is incorporated herein, in its entirety, by reference.

FIELD OF THE INVENTION

The invention generally relates to the human eye and, more particularly, the invention relates to the cornea of the human eye.

BACKGROUND OF THE INVENTION

The cornea consists of three regions, the epithelial sheet, the stroma, and the endothelial lining. The epithelial sheet is the outermost region. It consists of between five to eight layers of cells and makes up approximately 10% of the thickness of the cornea. Moreover, the epithelial sheet is renewable, in other words, capable of re-growth. In addition, the epithelial sheet is filled with thousands of tiny nerve endings, making the cornea extremely sensitive to pain when the epithelial sheet is, for example, scratched. The stroma is the middle region. It is located behind the epithelial sheet and makes up approximately 90% of the thickness of the stroma. The endothelial lining is the innermost region. It is a single layer of cells located behind the stroma.

During refractive eye surgery, the shape of the stroma is changed. For example, in Photo Refractive Keratectomy ("PRK") the shape of the stroma is changed with an excimer laser. First, however, the cells in the epithelial sheet are killed or removed using either a laser, a chemical, or a scraping device. After the PRK, the epithelial sheet grows back over the stroma. However, during this time period, the patient may experience pain and/or poor vision. In addition, regression might occur. Regression is the growth of the epithelial sheet in a pattern which restores, or nearly restores, the shape of the cornea prior to the PRK.

In Laser Assisted In Situ Keratomileusis ("LASIK"), the shape of the stroma is also changed using an excimer laser. In LASIK, a microkeratome is used to hinge back the outermost 20–30% of the cornea. The excimer laser is then used to change the shape of the exposed stroma. Because LASIK maintains the epithelial sheet, LASIK tends to avoid the problems discussed above in regard to PRK. However, LASIK is dependent on the use of the microkeratome, which may jam, shred, or lose the corneal "flap." Moreover, a suction device must be used in conjunction with the microkeratome, increasing intra ocular pressure up to approximately 100 mm Hg. For some vulnerable patients, the increase in intra ocular pressure can harm their eyes.

In Laser Epithelial Keratomileusis ("LASEK"), the epithelial sheet is loosened with an alcohol solution, then rolled back to expose the stroma. The excimer laser is then used to change the shape of the stroma and the loosened epithelial sheet is repositioned over the stroma. However, in LASEK, the patient experiences a slow return to clear vision and must wear a contact lens on the affected eye for a number of days. The slow return to clear vision is due to the use of the alcohol solution, which kills some of the epithelial cells. Moreover, the presence of dead epithelial cells renders the cornea vulnerable to infection, a situation that is enhanced because of the post-operative use of a contact lens.

SUMMARY OF THE INVENTION

In accordance with one embodiment of the invention, a method of delaminating the epithelial sheet of the cornea of a human eye comprises loosening the epithelial sheet with a loosening solution, the loosening solution including an agent, and separating the loosened epithelial sheet from the underlying tissue of the cornea. The agent may be hyaluronidase ACS. In particular, the agent may be a dose of hyaluronidase ACS between 30 International Units and 1000 International Units. In addition, the agent may be chondroitinase AC, chondroitinase ABC, keratanase, hyaluronidase, matrix metalloproteinase-1, matrix metalloproteinase-2, or matrix metalloproteinase-3. Further, the agent may be an activator of an endogenous enzyme that acts on the structure of the epithelial sheet.

In one embodiment of the invention, the process of loosening the epithelial sheet may include applying the loosening solution to the epithelial sheet of the cornea. For example, the loosening solution may be applied to the epithelial sheet using an eye well, in which the eye well is placed on the epithelial layer of the cornea and then the eye well is filled with the loosening solution. In an alternative embodiment of the invention, the loosening solution may be applied to the epithelial sheet using an absorbent material, in which the absorbent material is saturated with the loosening solution and then the absorbent material is placed on the epithelial sheet of the cornea. In a particular embodiment of the invention, the absorbent material may be a soft contact lens. After applying the loosening solution to the epithelial sheet of the cornea, the eye may be irrigated.

In these embodiments of the invention, when the loosening solution includes a dose of hyaluronidase ACS equal to 300 International Units, then the process of irrigating may occur substantially 90 seconds after the process of applying the loosening solution. In the alternative, when the loosening solution includes a dose of hyaluronidase ACS equal to 50 International Units, then the process of irrigating may occur substantially 120 seconds after the process of applying the loosening solution.

In an alternate embodiment of the invention, the process of loosening the epithelial sheet may include injecting the loosening solution into the top layer of the stroma. In the alternative, the process of loosening the epithelial sheet may include injecting the loosening solution into the middle layer of the stroma. In these embodiments of the invention, the loosening solution may include a dose of hyaluronidase ACS between 30 International Units and 50 International Units. In addition, the process of separating the loosened epithelial sheet may occur less than 180 seconds after the process of injecting the loosening solution.

In all of these embodiments of the invention, the process of separating the loosened epithelial sheet may include separating a portion of the loosened epithelial sheet. In addition, the process of separating the loosened epithelial sheet may include a traumatic separation. Atraumatic separation may include the use of a blunt edge, which may be attached to a vibrating system, or the use of a jet spray. The jet spray may be a jet of saline, water, or viscoelastic material. The process of separating the loosened epithelial sheet may further include the use of a physiological lubricant.

Further, the separated epithelial sheet may be placed back on the underlying tissue of the cornea. When replaced, a blood-clotting element may be applied to the epithelial sheet of the cornea to facilitate healing. In a particular embodiment of the invention, the blood-clotting element may be fibronectin. Moreover, the cornea may be anesthetized prior to the process of loosening the epithelial sheet.

In accordance with another embodiment of the invention, a method of delaminating the epithelial sheet from the cornea of a human eye comprises making an incision in the epithelial sheet, loosening the incised epithelial sheet using a loosening solution, the loosening solution including an agent, and separating the loosened epithelial sheet from the underlying tissue. In one embodiment of the invention, the incision is a circular incision, dividing the epithelial sheet into a first section inside the circular incision and a second section outside the circular incision. In this embodiment, the process of separating the loosened epithelial sheet includes dissecting the first section of the loosened epithelial sheet. In an alternate embodiment of the invention, the incision is a cruciate incision, dividing the epithelial sheet into four sections. In this alternate embodiment, the process of separating the loosened epithelial sheet includes rolling back the four sections of the loosened epithelial sheet. The process of separating the loosened epithelial sheet may also include separating at least a thin layer of the top layer of the stroma.

In accordance with a further embodiment of the invention, a method of administering a medicine through the epithelial sheet of the cornea of a human eye comprises applying a treatment solution of the medicine to the eye, the treatment solution including an agent. The agent may be hyaluronidase ACS. In particular, the agent may be a dose of hyaluronidase ACS between 30 International Units and 50 International Units. In addition, the treatment solution may include insulin. In the alternative, the treatment solution may include an antibiotic. In these embodiments, the process of applying a treatment solution may include the use of eye drops.

BRIEF DESCRIPTION OF THE DRAWINGS

The foregoing and other objects and advantages of the invention will be appreciated more fully from the following further description thereof with reference to the accompanying drawings wherein.

DETAILED DESCRIPTION OF THE INVENTION

In accordance with one embodiment of the invention, an agent is used to separate the epithelial sheet of the cornea from the underlying tissue of the cornea. The process, referred to as delaminating the epithelial sheet, leaves the epithelial sheet substantially intact and healthy. The process may be used in conjunction with various forms of eye surgery, e.g., refractive eye surgery, without concomitant pain or loss of vision due to the destruction, in whole or in part, of the epithelial sheet. In addition, the process may be used to aid the healing of a defective epithelial sheet.

Figure 1:
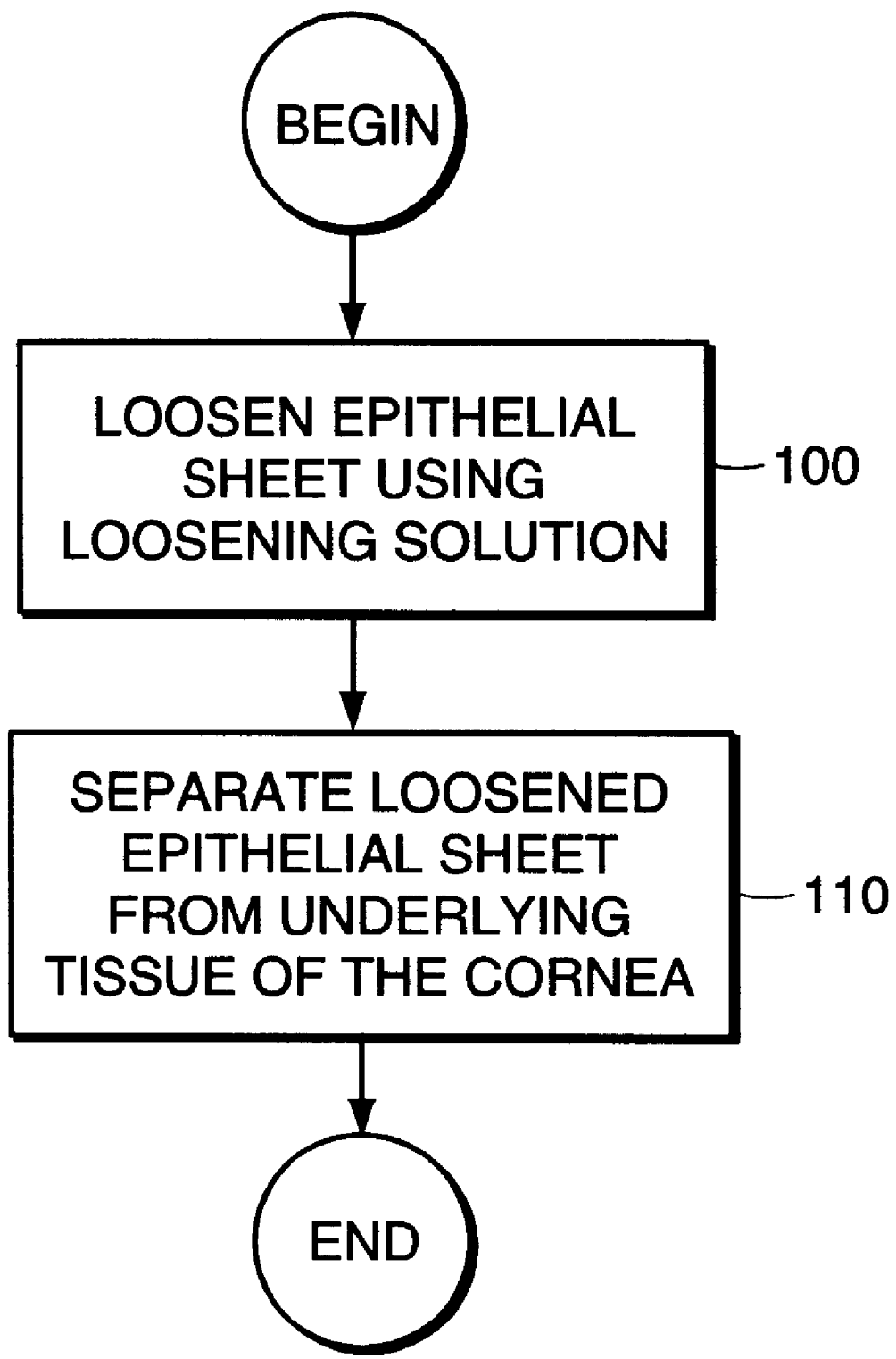
FIG. 1 shows an exemplary process for delaminating the epithelial sheet of the cornea of a human eye using an agent.

The agent used in the various embodiments of the invention is an agent that acts on the structural components of the epithelial sheet. For example, hyaluronidase ACS, as described in U.S. Pat. No. 5,866,120, the disclosure of which is incorporated herein, in its entirety, by reference, acts on the structural components of the epithelial sheet. In addition, chondroitinase AC, chondroitinase ABC, keratanase, matrix metalloproteinase-1, matrix metalloproteinase-2, matrix metalloproteinase-3, as well as other types of hyaluronidase, act on the structural components of the epithelial sheet. Further, the agent may an activator of an endogenous enzyme which, in turn, acts on the structural components of the epithelial sheet. For a discussion of one use of activators of endogenous enzymes in the human eye, refer to U.S. Pat. No. 5,626,865, the disclosure of which is incorporated herein, in its entirety, by reference, FIG. 1 shows an exemplary process for delaminating the epithelial sheet of the cornea of a human eye using an agent. The process begins at step 100, in which the epithelial sheet is loosened with a loosening solution, the loosening solution including an agent. The cornea may be anesthetized prior to the application of the loosening solution. The process concludes at step 110, in which the loosened epithelial sheet is separated from the underlying tissue of the cornea. For purposes of the invention, separated includes dissecting the epithelial sheet (in whole or in part), rolling back the epithelial sheet, or a combination of both procedures. In addition, separated may include separating, along with the epithelial sheet, at least a thin layer of the top layer of the stroma.

Figure 2A:
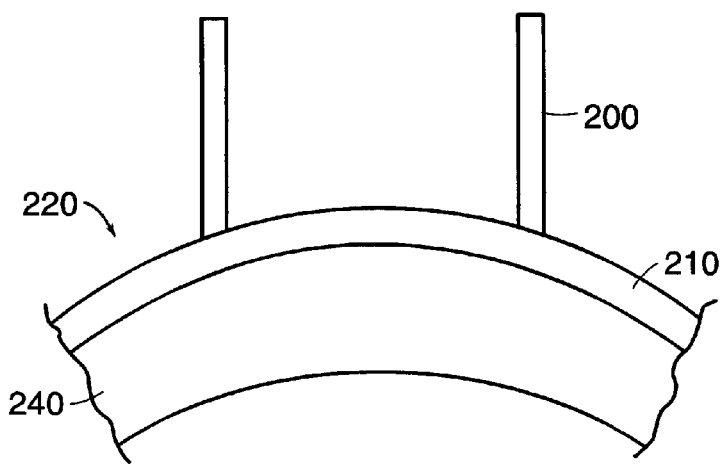
FIGS. 2a through 2c show an exemplary process for delaminating the epithelial sheet of the cornea of a human eye using an agent and an eye well.
Figure 2B:
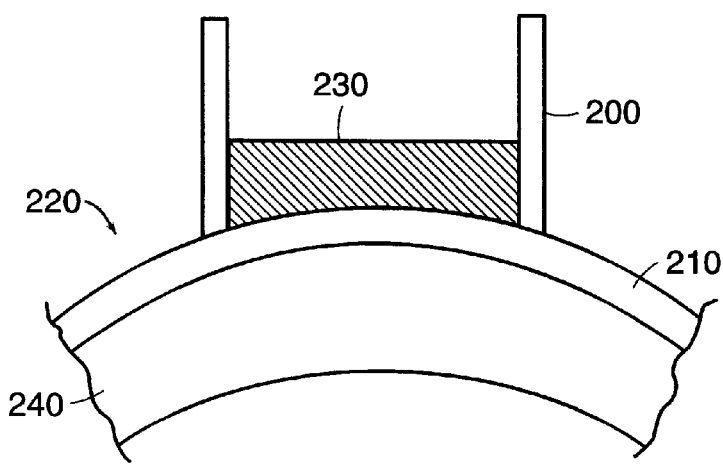
Figure 2C:
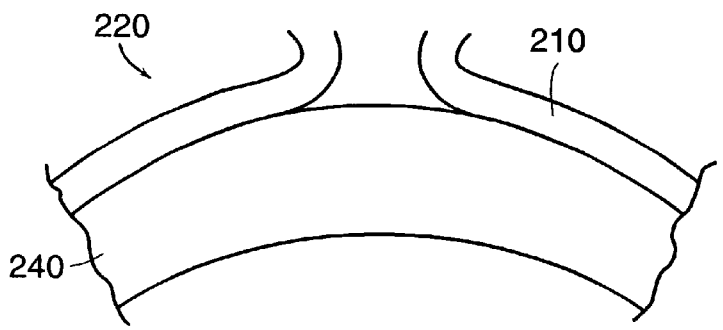

FIGS. 2a through 2c show an exemplary process for delaminating the epithelial sheet of the cornea of a human eye using an agent and an eye well. In this exemplary process, as shown in FIG. 2a, eye well 200 is first placed on epithelial sheet 210 of cornea 220. Then, as shown in FIG. 2b, eye well 200 is filled with loosening solution 230, loosening solution 230 including an agent. Next, eye well 200 is removed and the eye is irrigated, thereby flushing loosening solution 230 from the eye. Typically, the eye is irrigated with a saline solution. Last, as shown in FIG. 2c, loosened epithelial sheet 210 is separated from under lying tissue 240 of cornea 220. In FIG. 2c, loosened epithelial sheet 210 is being rolled back to expose a portion of underlying tissue 240. As noted above, loosened epithelial sheet 210 may also be dissected.

In an alternate embodiment of the invention, loosening solution 230 may be applied to epithelial sheet 210 via an absorbent material. In this alternate embodiment, an absorbent material is saturated with loosening solution 230 and then placed on epithelial sheet 210 of cornea 220. In a particular embodiment of this alternate embodiment, the absorbent material is a soft contact lens, which is first saturated with loosening solution 230 and then placed on the eye.

The amount of time loosening solution 230 remains in contact with epithelial sheet 210 is dependent upon the concentration of the agent used in loosening solution 230. For example, when the agent is a 300 International Unit ("IU") dose of, for example, hyaluronidase ACS, then loosening solution 230 remains in contact with epithelial sheet 210 for substantially 90 seconds. In the alternative, when the agent is a 50 IU dose of, for example, hyaluronidase ACS, then loosening solution 230 remains in contact with epithelial sheet 210 for substantially 120 seconds. Using routine experimentation, a person of skill in the art can determine, based on the concentration of the agent used in loosening solution 230, the effective amount of time loosening solution 230 should remain in contact with epithelial sheet 210.

In another alternate embodiment of the invention, loosening solution 230 may be injected into the stroma of cornea 220. For example, loosening solution 230 may be injected into the top layer of the stroma of cornea 220. In the alternative, loosening solution 230 may be injected into the middle layer of the stroma of cornea 220. In this alternate embodiment, the eye does not need to be irrigated because loosening solution 230 is not topically applied to the eye.

When injecting loosening solution 230, the concentration of the agent may vary from the concentration of the same agent topically applied to the eye. For example, when topically applying hyaluronidase ACS, the concentration of hyaluronidase ACS in loosening solution 230 may range from a 30 IU dose of hyaluronidase ACS to a 1000 IU dose of hyaluronidase ACS. In contrast, when injecting hyaluronidase ACS, the concentration of hyaluronidase ACS in loosening solution 230 may range from a 30 IU dose of hyaluronidase ACS to a 50 IU dose of hyaluronidase ACS. Loosening solution 230 may, however, include a higher dose of hyaluronidase ACS. In regard to the amount of time needed prior to beginning the process of separating epithelial sheet 210 from underlying tissue 240, the process may be started within minutes of the injection. Typically, the process of separating is started less than 180 seconds after the injection of loosening solution 230.

Epithelial sheet 210 may be separated using several atraumatic procedures. For example, epithelial sheet 210 may be separated using a blunt edge made of either metal or plastic. In addition, the blunt edge may be stationary or attached to a vibrating system. If needed, a physiological lubricant may be used to facilitate the separation.

A further atraumatic procedure for separating epithelial sheet 210 includes the use of a jet spray. The jet spray may be a jet of saline or water. In the alternative, the jet spray may be a slower jet, relative to the jet of saline or water, of viscoelastic material.

If separated epithelial sheet 210 is to be placed back on underlying tissue 240 after, for example, the shape of the stroma of cornea 220 is changed using an excimer laser, separated epithelial sheet 210 should be kept moist and, thereby, healthy while separated from underlying tissue 240. Once separated epithelial sheet 210 is placed back on underlying tissue 240, a blood-clotting element, e.g., fibronectin, may be applied to replaced epithelial sheet 210 to facilitate healing.

Figure 3A:
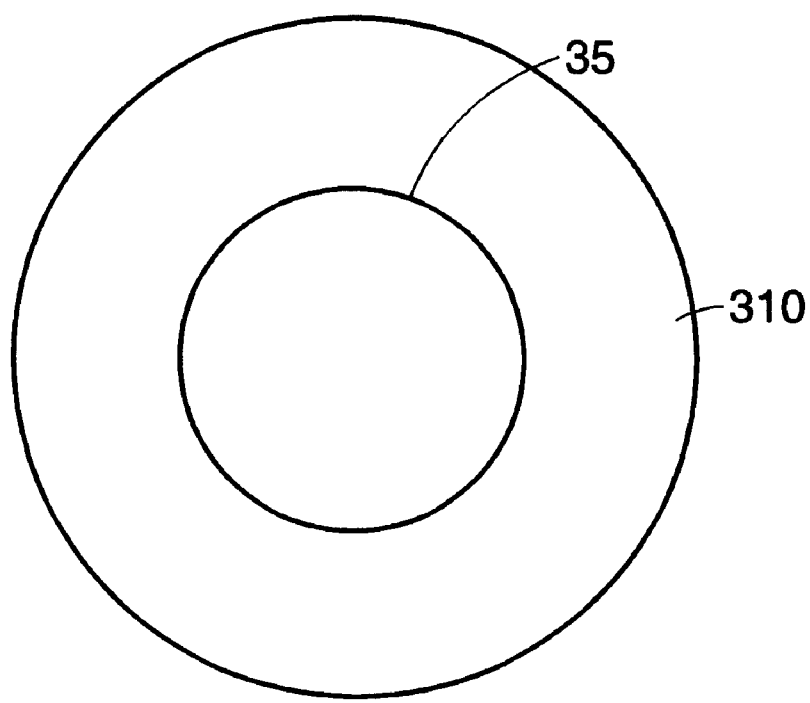
FIGS. 3a and 3b show another exemplary process for delaminating the epithelial sheet of the cornea of a human eye using an agent.
Figure 3B:
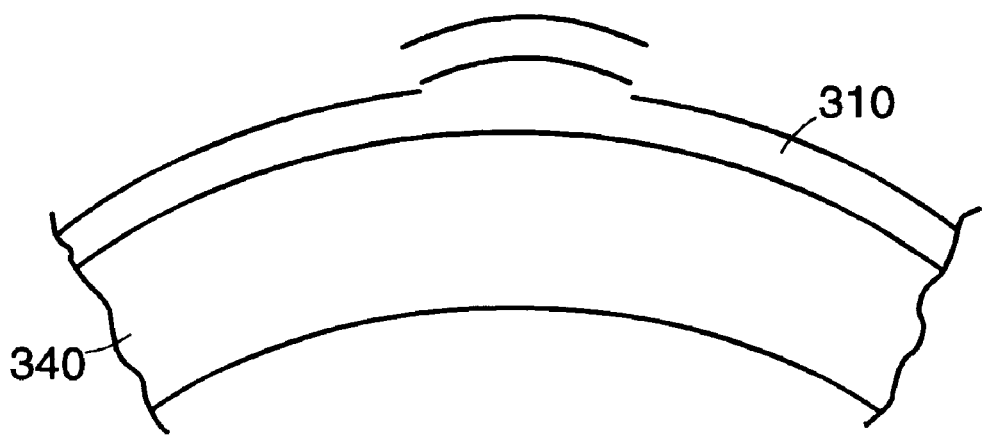

FIGS. 3a and 3b show another exemplary process for delaminating the epithelial sheet of the cornea of a human eye using an agent. In this exemplary process, as shown in FIG. 3a, an incision is first made in epithelial sheet 310. In FIG. 3a, circular incision 35 is made in epithelial sheet 310. Then, epithelial sheet 310 is loosened, for example, by injecting a loosening solution into the top layer of the cornea's stroma. Next, as shown in FIG. 3b, loosened epithelial sheet 310 is dissected using, for example, a blunt edge. As discussed above, if loosened epithelial sheet 310 will be placed back on underlying tissue 340, then loosened epithelial sheet 310 should be kept moist while separated from underlying tissue 340.

Figure 4A:
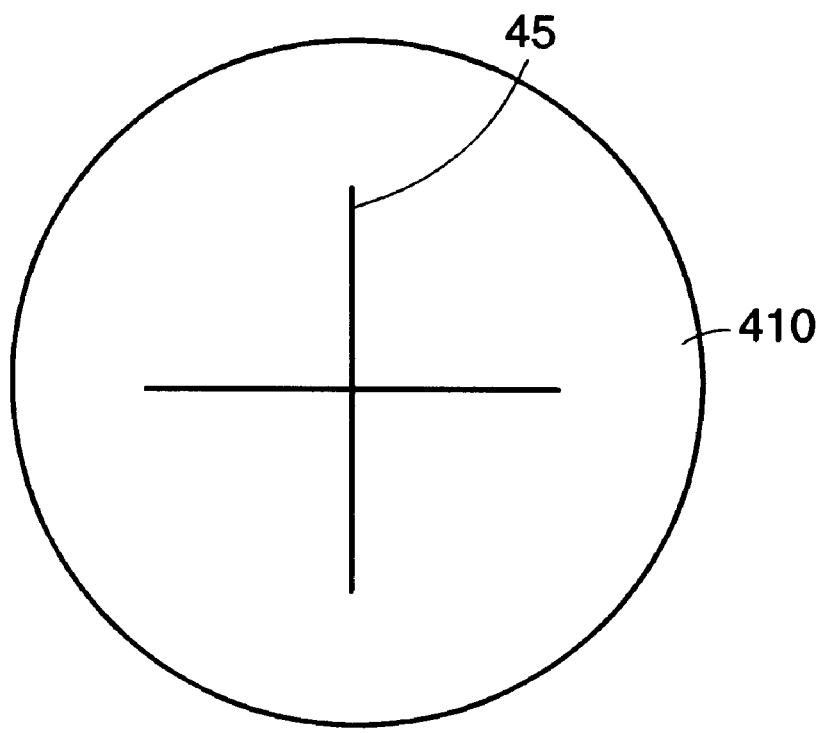
FIGS. 4a and 4b show still another exemplary process for delaminating the epithelial sheet of the cornea of a human eye using an agent.
Figure 4B:
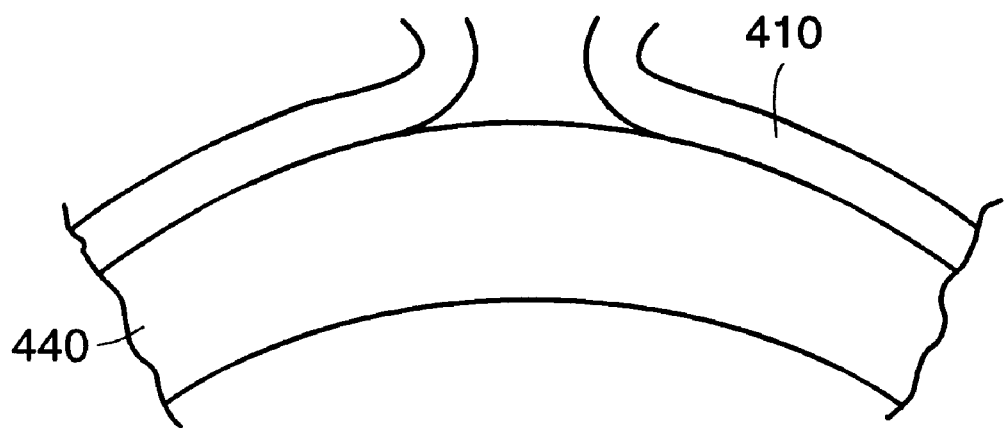

FIGS. 4a and 4b; show still another exemplary process for delaminating the epithelial sheet of the cornea of a human eye using an agent. In this exemplary process, as shown in FIG. 4a, cruciate incision 45 is first made in epithelial sheet 410. Then, epithelial sheet 410 is loosened, for example, by saturating a soft contact lens with a loosening solution and placing the soft contact lens on the eye. Next, the eye is irrigated. Then, as shown in FIG. 4b, loosened epithelial sheet 410 is rolled back using, for example, a jet spray. While separated from underlying tissue 440, loosened epithelial sheet 410 should be kept moist. Last, loosened epithelial sheet 410 is rolled back into place over underlying tissue 440 using, for example, a blunt edge. As noted above, a blood-clotting element may be applied to replaced epithelial sheet 410 to facilitate healing.

In accordance with another embodiment of the invention, an agent is used to administer medicine through the epithelial sheet of the cornea of a human eye. As discussed above, the agent used in the various embodiments of the invention is an agent that acts on the structural components of the epithelial sheet.

Figure 5:
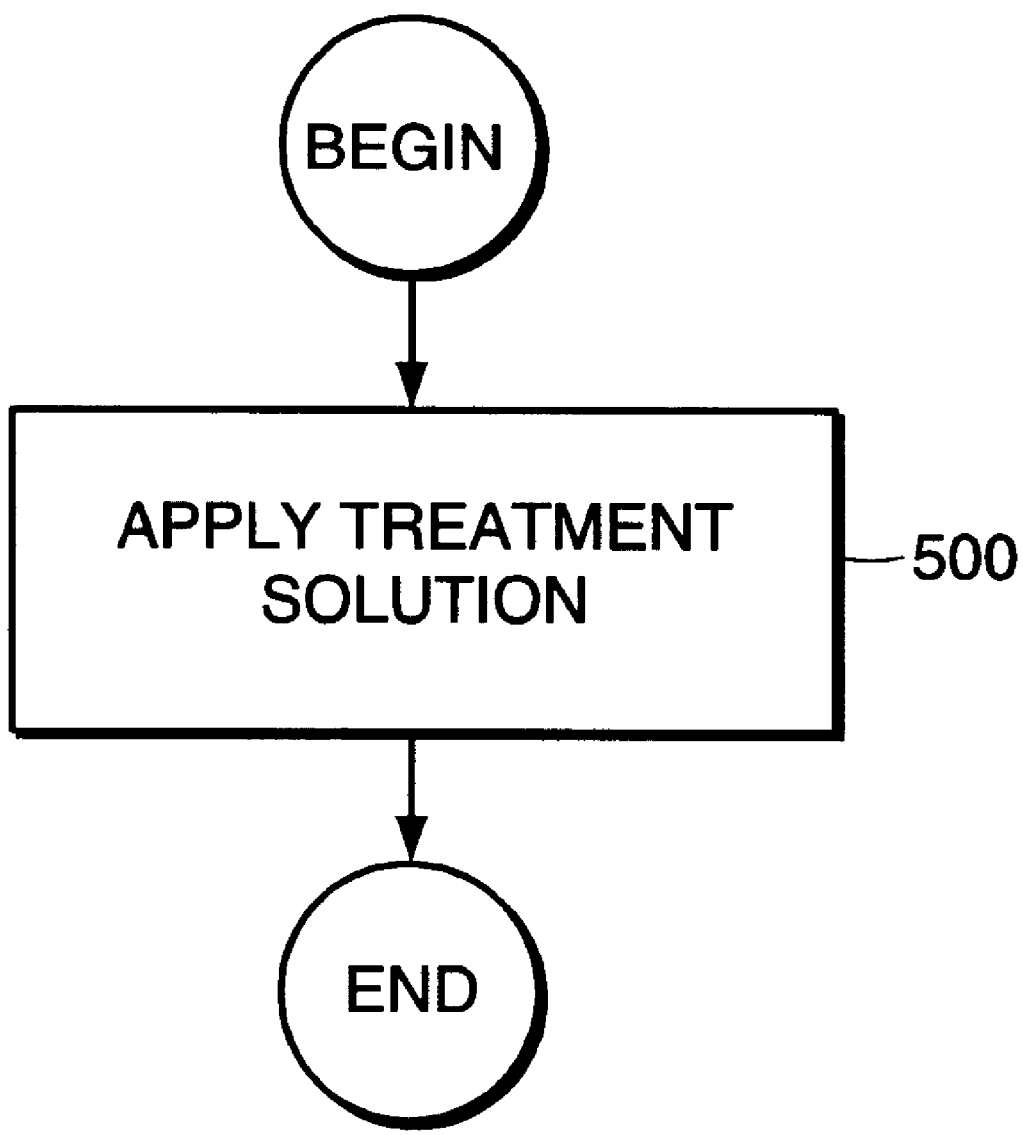
FIG. 5 shows an exemplary process for administering a medicine through the epithelial sheet of the cornea of a human eye using an agent.

FIG. 5 shows an exemplary process for administering a medicine through the epithelial sheet of the cornea of a human eye using an agent. In the process, as shown in step 500, a treatment solution of medicine is applied to the eye, the treatment solution including an agent. The concentration of the agent in the treatment solution is dependent upon the agent. For example, when the agent is hyaluronidase ACS, the concentration of hyaluronidase ACS in the treatment solution may range from a 30 International Unit ("IU") dose of hyaluronidase ACS to a 50 IU dose of hyaluronidase ACS. The treatment solution may be applied to the eye via eye drops. The medicine being administered may include, for example, insulin or an antibiotic.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

I claim:

1. A method of delaminating the epithelial sheet of the cornea of a human eye, the cornea having underlying tissue, the underlying tissue including a stroma, the stroma having a top layer and a middle layer, the method comprising:

loosening the epithelial sheet with a loosening solution, the loosening solution including an agent; and separating the loosened epithelial sheet from the underlying tissue of the cornea.

2. The method according to claim 1 wherein the agent is hyaluronidase ACS.

3. The method according to claim 2 wherein the agent is a dose of hyaluronidase ACS between 30 International Units and 1000 International Units.

4. The method according to claim 1 wherein the agent is selected from the group consisting of chondroitinase AC, chondroitinase ABC, keratanase, hyaluronidase, matrix metalloproteinase-1, matrix metalloproteinase-2, and matrix metalloproteinase-3.

5. The method according to claim 1 wherein the agent is an activator of an endogenous enzyme that acts on the structure of the epithelial sheet.

6. The method according to claim 1 wherein the process of loosening the epithelial sheet includes applying the loosening solution to the epithelial sheet of the cornea.

7. The method according to claim 6 wherein the process of loosening the epithelial sheet further comprises:

irrigating the eye.

8. The method according to claim 6 wherein the process of applying the loosening solution further comprises:

placing an eye well on the epithelial sheet of the cornea; and filling the eye well with the loosening solution.

9. The method according to claim 6 wherein the process of applying the loosening solution further comprises:

saturating an absorbent material with the loosening solution; and placing the absorbent material on the epithelial sheet of the cornea.

10. The method according to claim 9 wherein the absorbent material is a soft contact lens.

11. The method according to claim 7 wherein the agent is a dose of hyaluronidase ACS equal to 300 International Units and the process of irrigating occurs substantially 90 seconds after the process of applying the loosening solution.

12. The method according to claim 7 wherein the agent is a dose of hyaluronidase ACS equal to 50 International Units and the process of irrigating occurs substantially 120 seconds after the process of applying the loosening solution.

13. The method according to claim 1 wherein the process of loosening the epithelial sheet includes injecting the loosening solution into the top layer of the stroma.

14. The method according to claim 1 wherein the process of loosening the epithelial sheet includes injecting the loosening solution into the middle layer of the stroma.

15. The method according to claim 13 or claim 14 wherein the agent is a dose of hyaluronidase ACS between 30 International Units and 50 International Units.

16. The method according to claim 15 wherein the process of separating the loosened epithelial sheet occurs less than 180 seconds after the process of injecting the loosening solution.

17. The method according to claim 1 wherein the process of separating the loosened epithelial sheet includes separating a portion of the loosened epithelial sheet.

18. The method according to claim 1 wherein the process of separating the loosened epithelial sheet includes atraumatic separation.

19. The method according to claim 18 wherein atraumatic separation includes the use of a blunt edge.

20. The method according to claim 19 wherein the blunt edge is attached to a vibrating system.

21. The method according to claim 18 wherein atraumatic separation includes the use of a jet spray.

22. The method according to claim 21 wherein the jet spray is a jet of saline.

23. The method according to claim 21 wherein the jet spray is a jet of water.

24. The method according to claim 21 wherein the jet spray is a jet of viscoelastic material.

25. The method according to claim 1 wherein the process of separating the loosened epithelial sheet includes the use of a physiological lubricant.

26. The method according to claim 1, further comprising:

placing the separated epithelial sheet back on the underlying tissue of the cornea.

27. The method according to claim 26, further comprising:

applying a blood-clotting element to the epithelial sheet of the cornea.

28. The method according to claim 27 wherein the blood-clotting element is fibronectin.

29. The method according to claim 1 wherein the cornea is anesthetized prior to the process of loosening the epithelial sheet.

30. A method of delaminating the epithelial sheet from the cornea of a human eye, the cornea having underlying tissue, the underlying tissue including a stroma, the stroma having a top layer and a middle layer, the method comprising:

making an incision in the epithelial sheet;

loosening the incised epithelial sheet using a loosening solution, the loosening solution including an agent; and separating the loosened epithelial sheet from the underlying tissue of the cornea.

31. The method according to claim 30 wherein the incision is a circular incision, the circular incision dividing the epithelial sheet into a first section inside the circular incision and a second section outside the circular incision.

32. The method according to claim 31 wherein the process of separating the loosened epithelial sheet includes dissecting the first section of the loosened epithelial sheet.

33. The method according to claim 30 wherein the incision is a cruciate incision, the cruciate incision dividing the epithelial sheet into four sections.

34. The method according to claim 33 wherein the process of separating the loosened epithelial sheet includes rolling back the four sections of the loosened epithelial sheet.

35. The method according to claim 30 wherein the process of separating the loosened epithelial sheet includes separating at least a thin layer of the top layer of the stroma.

36. A method of administering a medicine through the epithelial sheet of the cornea of a human eye, the method comprising:

applying a treatment solution of the medicine to the eye, the treatment solution including an agent.

37. The method according to claim 36 wherein the agent is hyaluronidase ACS.

38. The method according to claim 37 wherein the agent is a dose of hyaluronidase ACS between 30 International Units and 50 International Units.

39. The method according to claim 36 wherein the treatment solution includes insulin.

40. The method according to claim 36 wherein the treatment solution includes an antibiotic.

41. The method according to claim 36 wherein the process of applying a treatment solution includes the use of eye drops.

* * * * *